United States Patent [19]

Matsuno

[11] Patent Number: 5,562,600
[45] Date of Patent: Oct. 8, 1996

[54] ENDOSCOPE

[75] Inventor: Shinichi Matsuno, Tokyo, Japan

[73] Assignee: Asahi Kogaku Kogyo Kabushiki Kaisha, Tokyo, Japan

[21] Appl. No.: 475,088

[22] Filed: Jun. 7, 1995

[30]   Foreign Application Priority Data

Jun. 13, 1994  [JP]  Japan .................................. 6-130179
Mar. 17, 1995  [JP]  Japan .................................. 7-058515

[51] Int. Cl.⁶ ...................................................... A61B 1/00
[52] U.S. Cl. ............................................................ 600/107
[58] Field of Search ..................................... 600/101, 107, 600/129, 146, 153, 154, 170; 606/19

[56]   References Cited

U.S. PATENT DOCUMENTS

| | | |
|---|---|---|
| 4,407,273 | 10/1983 | Ouchi . |
| 4,436,087 | 3/1984 | Ouchi . |
| 4,593,680 | 6/1986 | Kubokawa ............................ 600/107 |
| 4,706,655 | 11/1987 | Krauter ................................ 600/106 |
| 4,841,949 | 6/1989 | Shimizu et al. ....................... 600/107 |
| 4,924,852 | 5/1990 | Suzuki et al. ........................ 600/107 X |
| 5,460,168 | 10/1995 | Masubuchi et al. ................. 600/107 X |

FOREIGN PATENT DOCUMENTS 54-90088  6/1979  Japan .
4218134  8/1992  Japan .

Primary Examiner—Linda C. Dvorak
Assistant Examiner—David R. Risley
Attorney, Agent, or Firm—Greenblum & Bernstein P.L.C.

[57]   ABSTRACT

An endoscope having a tool guide member which is pivotable in the longitudinal direction of an insert part of the endoscope by remote control to change the direction of projection of a tool for an endoscopic procedure, which is projected outwardly from the distal end of the insert part. A pair of inner and outer walls are formed on the distal end of the insert part so as to be in contact with both side surfaces of the tool guide member. A control wire is driven to move back and forth by remote control to pivot the tool guide member. The distal end of the control wire is disposed at the outside of the outer wall. A driving force transmitting member is disposed to extend through a bore formed in the outer wall so as to transmit the motion of the control wire to the tool guide member.

12 Claims, 5 Drawing Sheets

ENDOSCOPE

BACKGROUND OF THE INVENTION

The present disclosure relates to subject matter contained in Japanese Patent Application No. 6-130179 (filed on Jun. 13, 1994) and Japanese Patent Application No. 7-58515 (filed on Mar. 17, 1995), which are expressly incorporated herein by reference in their entireties.

1. Field of the Invention

The present invention relates to an endoscope having a tool guide member for changing the direction of projection of a bioptic forceps or other tool for an endoscopic procedure (hereinafter referred to as "tool"), which is projected outwardly from the distal end of the insert part of the endoscope.

2. Description of the Prior Art

The tool guide member of an endoscope is generally disposed at the distal end of the insert part of the endoscope so as to be pivotable about a shaft, and pivoted by a control wire which is remote-controlled.

FIG. 7 shows the distal end of an insert part of a conventional endoscope, with a plastic cover detached therefrom. The endoscope has a distal end block 51 which is provided at the distal end of the insert part. The distal end block 51 has a viewing window 52 and an illuminating window 53, which are provided in one of side portions of the distal end block 51. A tool guide member 54 is provided in the other side portion to change the direction of projection of a tool, which is projected sidewardly.

The distal end block 51 has a pair of inner and outer walls 55 and 56 which are in contact with both side surfaces of the tool guide member 54. The tool guide member 54 pivots about a shaft 57 which is inserted at both ends thereof into the two walls 55 and 56.

The outer wall 56 is provided with a relatively large cut portion 59 so as not to interfere with a stopper pin 58 which projects from the side surface of the tool guide member 54. A control wire 60 for pivoting the tool guide member 54 by remote control extends through the cut portion of the outer wall 56, and the distal end of the control wire 60 is connected to the side surface of the tool guide member 54.

In the endoscope having the above-described structure, however, a relatively large gap is formed between the cut wall portion 59 and the control wire 60. Accordingly, as shown in FIG. 8, when a tool 100 is to be projected outwardly along the tool guide member 54 from a tool inserting channel 62, the distal end of the tool 100 may enter the gap between the control wire 60 and the cut wall portion 59 to get caught on the control wire 60, resulting in a failure to control the tool 100. Reference numeral 61 in FIG. 8 denotes a plastic cover which covers the distal end block 51.

There is a conventional endoscope in which the outer wall 56 is formed to extend as close to the control wire 60 as possible, thereby minimizing the gap (Japanese Patent Unexamined Publication (KOKAI) No. 4-218134). The conventional technique can cope with the above-described problem to a certain extent. However, when a tool with a thin distal end is used, it is likely that the thin distal end will get caught in the gap between the control wire 60 and the outer wall 56.

There is another conventional endoscope in which the control wire is disposed at the inside of the inner wall so as to be separate from the tool guide member (Japanese Utility Model Unexamined Publication (KOKAI) No. 54-90088).

With this arrangement, however, the control wire lies between the viewing window and the tool guide member, and the tool guide member lies correspondingly far away from the viewing window. As a result, the tool guide member can be seen only at an edge of the observation field of view. Therefore, the tool guiding performance deteriorates to a considerable extent.

SUMMARY OF THE INVENTION

An object of the present invention is to provide an endoscope which is designed so that, even when a tool for an endoscopic procedure which has a thin distal end, the tool can be projected smoothly along the tool guide member without getting caught on the control wire, and that it is possible to guide a tool for an endoscopic procedure with ease while observing it in the central portion of the observation field of view.

Other objects and advantages of the present invention will become apparent from the following detailed description of an illustrated embodiment of the invention.

According to the present invention, there is provided an endoscope having a viewing window which is disposed in one of side portions of the distal end of an insert part of the endoscope, and a tool guide member which is disposed in the other side portion so as to be pivotable in the longitudinal direction of the insert part by remote control to change the direction of projection of a tool for an endoscopic procedure, which is projected outwardly from the distal end of the insert part. The endoscope includes a pair of inner and outer walls which are formed on the distal end of the insert part so as to be in contact with both side surfaces of the tool guide member, and a control wire which is driven to move back and forth by remote control. The distal end of the control wire is disposed at the outside of the outer wall. The endoscope further includes a driving force transmitting member which is disposed to extend through the outer wall so as to transmit the motion of the control wire to the tool guide member.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

One embodiment of the present invention will be described below with reference to the accompanying drawings.

Figure 1:
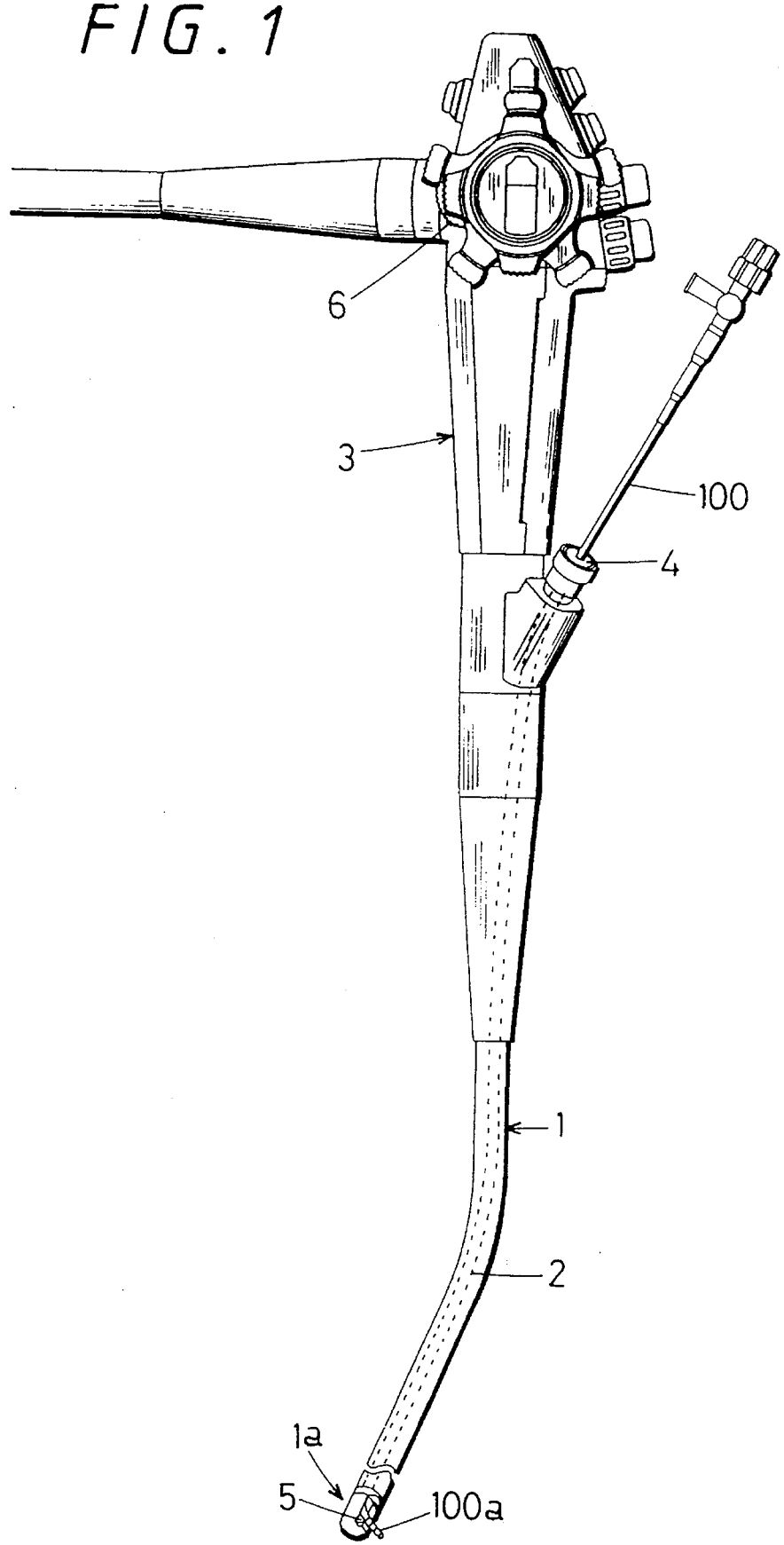
FIG. 1 is a side view showing the whole arrangement of one embodiment of the endoscope according to the present invention.

FIG. 1 shows one embodiment of the endoscope according to the present invention. The endoscope has a flexible insert part 1. A tool inserting channel 2 extends through the insert part 1 over the entire length thereof. The tool inserting channel 2 is made of a tetrafluoroethylene resin tube, for example.

A control part 3 is connected to the proximal end of the insert part 1. A tool inlet 4 projects from a position near the joint of the insert part 1 and the control part 3. The proximal end of the tool inserting channel 2 is connected to the tool inlet 4. The distal end of the tool inserting channel 2 is connected to a distal end part 1a of the insert part 1.

Bioptic forceps and various other tools 100 may be inserted into the tool inserting channel 2. In this embodiment, a liquid supply tube for supplying a contrast medium or other liquid is employed as an example of the tool 100.

The distal end 100a of the tool 100 projects sidewardly from the distal end part 1a of the insert part 1. A tool guide member 5 for changing the direction of projection of the distal end 100a of the tool 100 is incorporated in the distal end part 1a of the insert part 1. The tool guide member 5 is pivoted by a control wire which is driven to move back and forth in response to the operation of a control knob 6 which is provided on the control part 3. It should be noted that "front" means the insert part distal end side, and "rear" means the insert part proximal end side.

Figure 2:
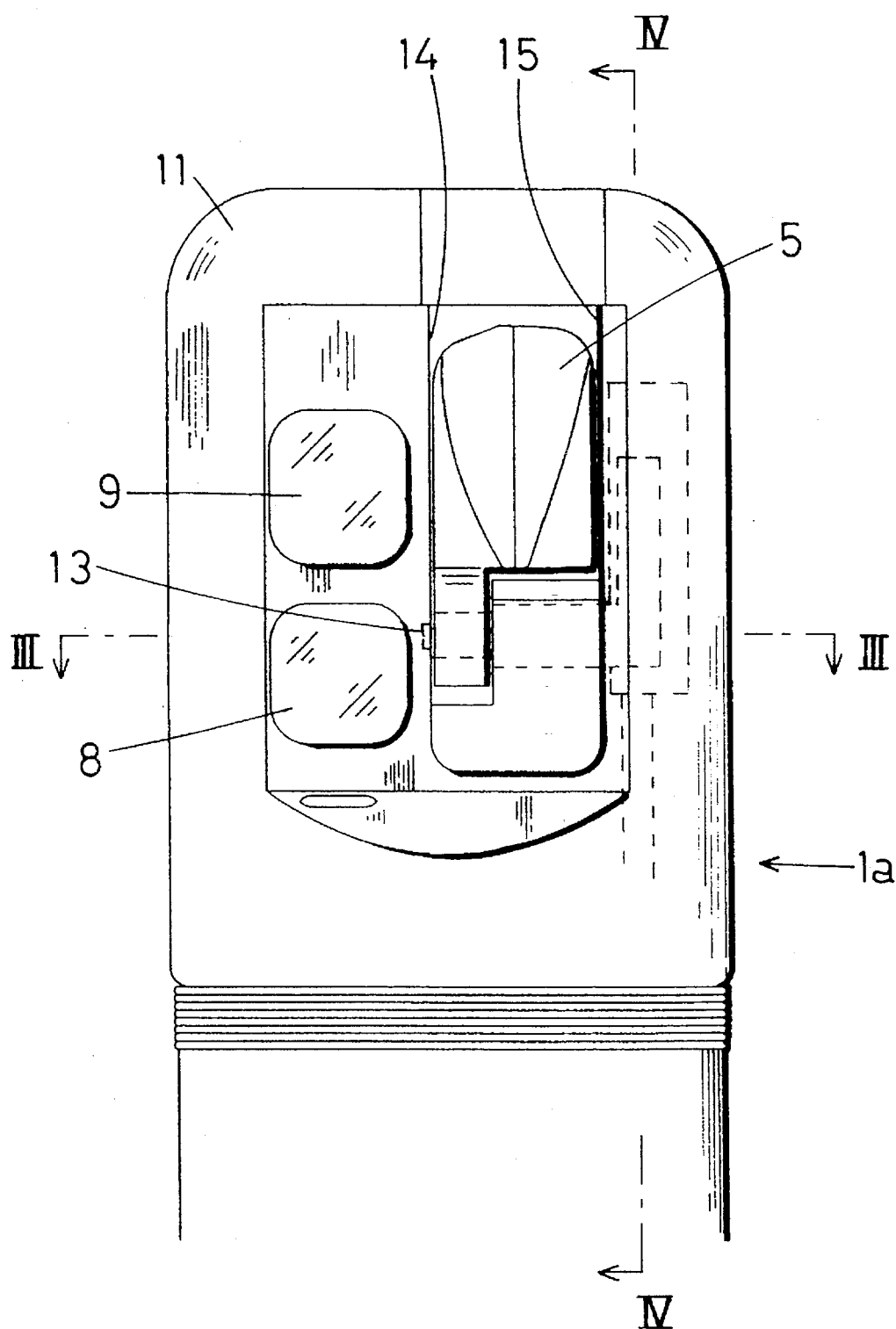
FIG. 2 is a plan view showing a distal end part of the embodiment of the present invention.

FIG. 2 is a plan view of the distal end part 1a of the insert part 1. A viewing window 8 and an illuminating window 9 are provided in the left-hand half of a side of the distal end part 1a. The two windows 8 and 9 are disposed in side-by-side relation to each other in the longitudinal direction of the distal end part 1a. The tool guide member 5 is disposed in the right-hand half of the distal end part 1a so as to be pivotable longitudinally.

Figure 3:
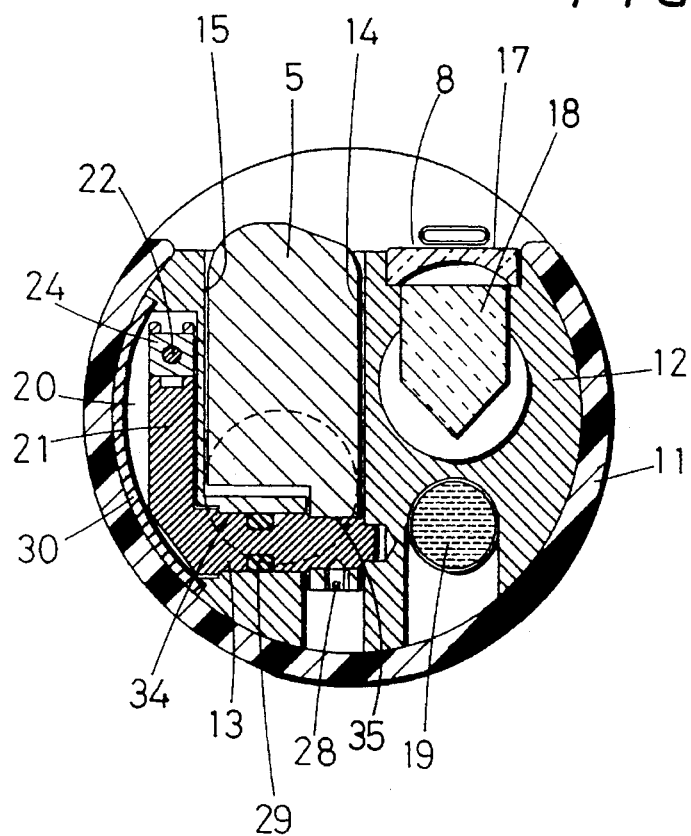
FIG. 3 is a sectional view taken along the line III—III in FIG. 2, showing the embodiment of the present invention.
Figure 4:
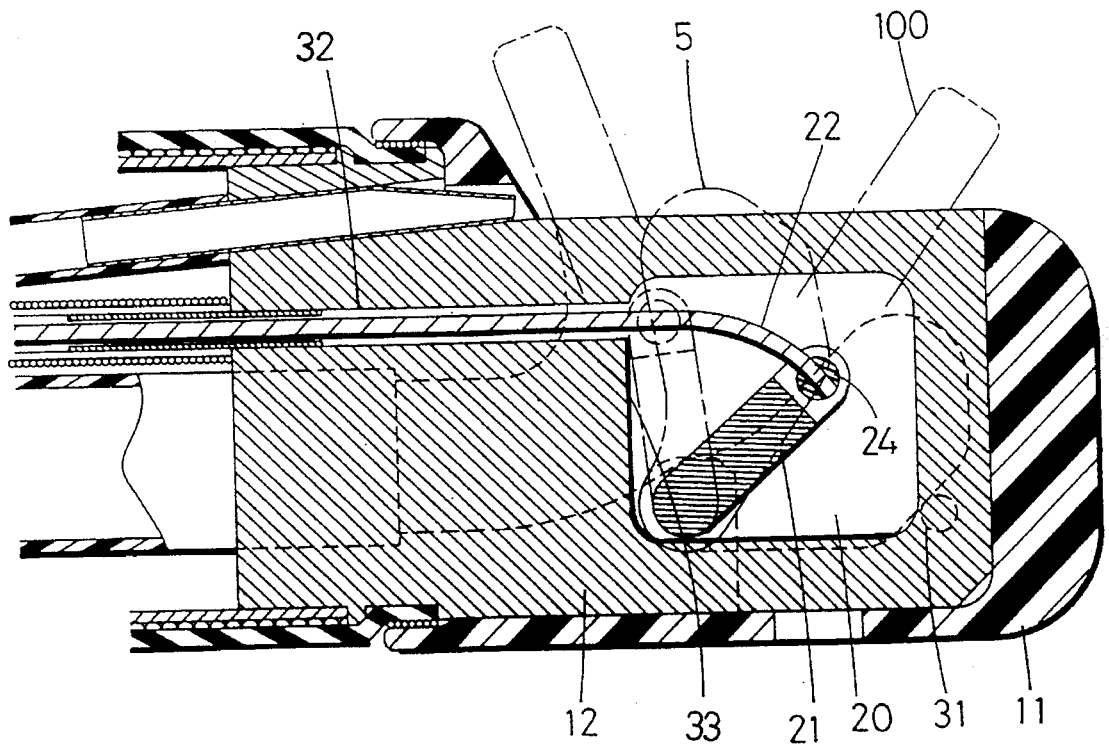
FIG. 4 is a sectional view taken along the line IV—IV in FIG. 2, showing the embodiment of the present invention.
Figure 5:
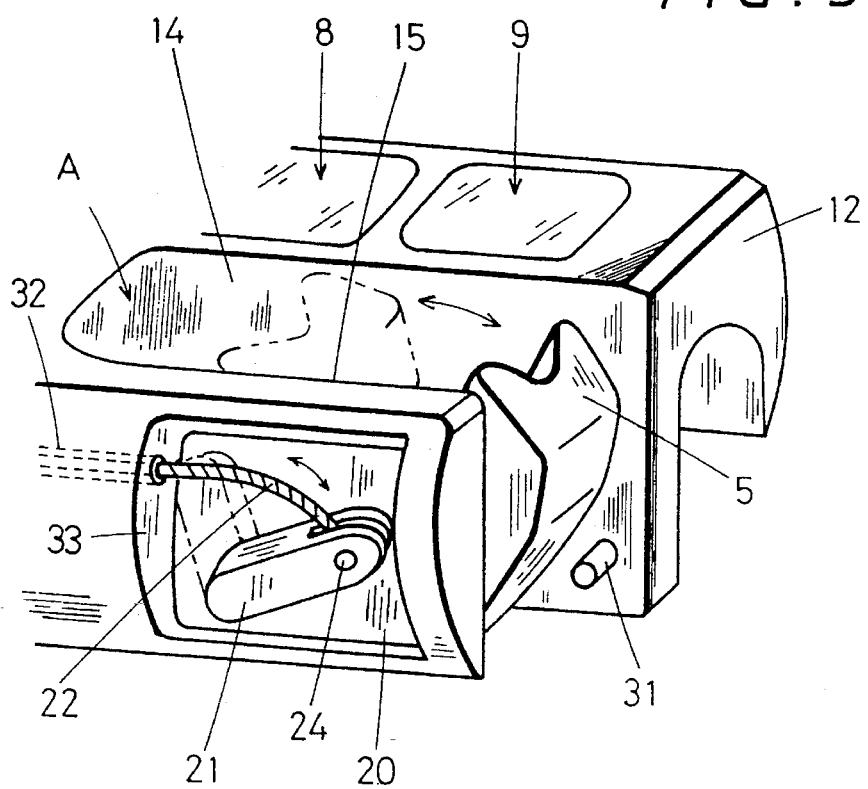
FIG. 5 is a perspective view showing the distal end part of the endoscope according to the embodiment of the present invention, with a plastic cover detached therefrom.

FIG. 3 is a sectional view taken along the line III—III in FIG. 2, and FIG. 4 is a sectional view taken along the line IV—IV in FIG. 2. FIG. 5 shows the distal end part 1a of the insert part 1, with a plastic cover 11 detached therefrom.

The distal end part 1a of the insert part 1 is formed by attaching various constituent elements to a distal end block 12 which is made of a stainless steel. The distal end part 1a is covered with an electrically insulating plastic cover 11 except for an outer peripheral portion thereof which corresponds to an area in which the viewing and illuminating windows 8 and 9 are present and the tool 100 projects.

As shown in FIG. 3, a cover lens 17 is attached to the viewing window 8, and a rectangular roof prism 18 is disposed at the inner side of the cover lens 17. A light guide fiber bundle 19 is provided so that an exit end surface thereof is disposed at the inner side of the illuminating window 9.

The tool guide member 5 rotates about a guide member driving shaft 13 which is provided perpendicularly to the longitudinal direction of the distal end part 1a, thereby pivoting back and forth. The distal end block 12 has a pair of parallel inner and outer walls 14 and 15 which are in contact with both side surfaces of the tool guide member 5 within the pivoting range of the tool guide member 5.

The inner wall 14 lies adjacent to the viewing window 8. Accordingly, the tool 100 that is projected along the tool guide member 5 can be observed in the central portion of the observation field of view which is obtained through the viewing window 8.

The outer wall 15 is formed so that the upper end thereof is approximately flush with the surfaces of the viewing and illuminating windows 8 and 9 in the same way as in the case of the inner wall 14. In other words, no portion of the outer wall 15 is cut. The control wire 22 lies at the outside of the wall surface of the outer wall 15.

Accordingly, the tool 100 that is projected along the tool guide member 5 is completely isolated from the control wire 22 by the outer wall 15. There is therefore no possibility of the tool 100 getting caught on the control wire 22.

A guide member driving chamber 20 is formed in a substantially quadrangular recess which is defined at the outside of the outer wall 15. The bottom surface of the guide member driving chamber 20 is parallel to the mutually opposing wall surfaces of the inner and outer walls 14 and 15. A guide member driving lever 21 is accommodated in the guide member driving chamber 20. The guide member driving lever 21 is integrally connected to the guide member driving shaft 13 so as to extend at right angles to the axis of the driving shaft 13.

The distal end portion of the control wire 22 is drawn into the guide member driving chamber 20 through a bore 32 formed in the outer wall 15 from the rear side thereof, and connected to the upper end portion of the guide member driving lever 21 in the guide member driving chamber 20.

Figure 6:
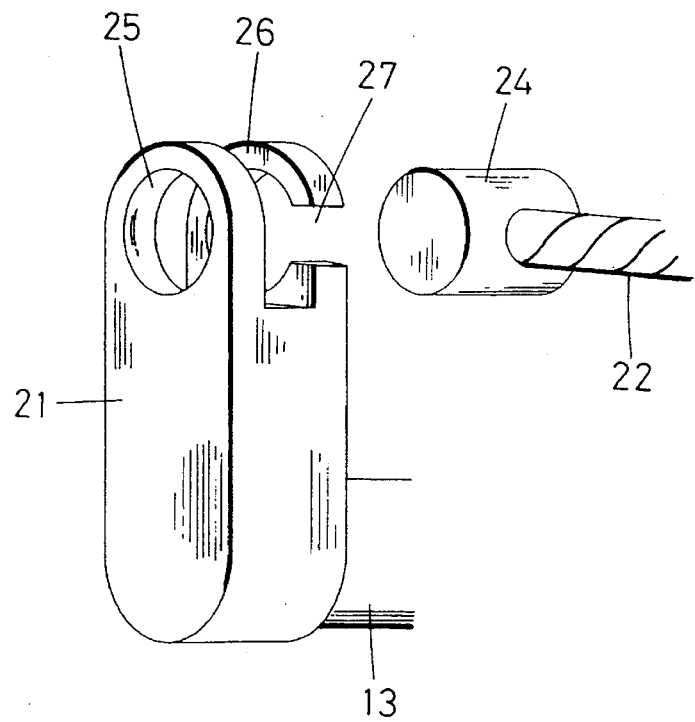
FIG. 6 is an enlarged perspective view of a control wire connecting part in the embodiment of the present invention.
Figure 7:
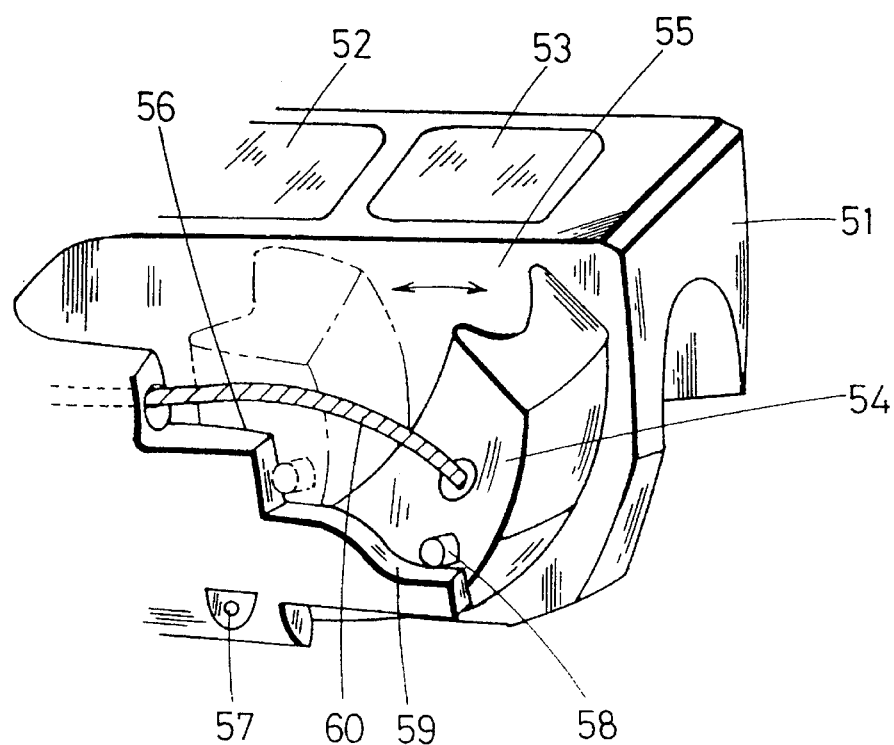
FIG. 7 is a perspective view showing a distal end part of a conventional endoscope, with a plastic cover detached therefrom.
Figure 8:
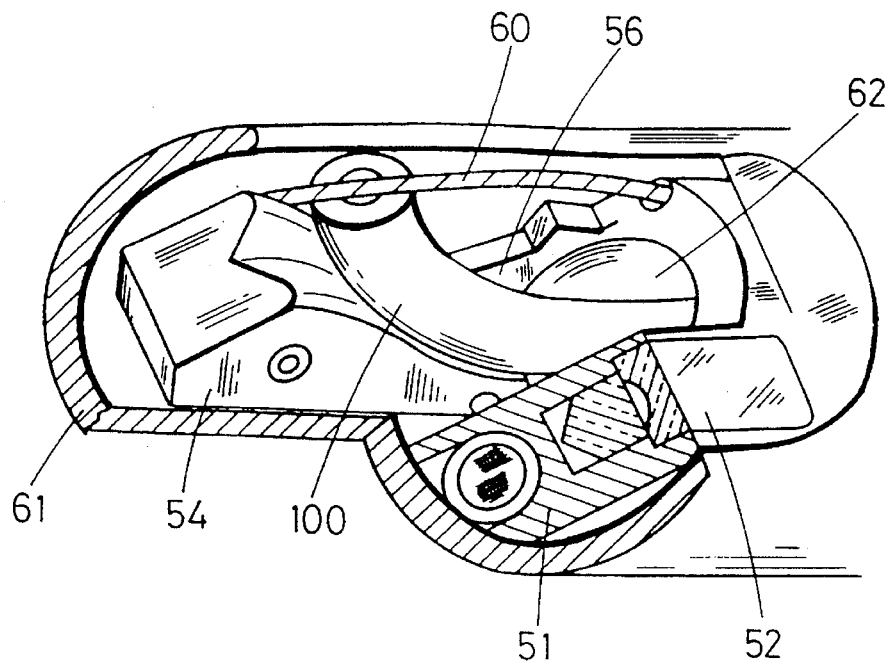
FIG. 8 is a partly-sectioned perspective view of the distal end part of the conventional endoscope.

FIG. 6 shows the joint of the control wire 22 and the guide member driving lever 21. A pin 24 is rigidly brazed to the end of the control wire 22 such that the pin 24 and the control wire 22 form a T-shape. The guide member driving lever 21 is provided with a bore 25 into which the pin 24 is inserted.

Further, a groove 26 is formed in the center of the upper end of the guide member driving lever 21 so that the driving lever 21 will not interfere with the control wire 22. Thus, the control wire 22 can be drawn out in any direction. The guide member driving lever 21 is further provided with a slit 27 for passing the control wire 22 so that the pin 24 can be inserted into the bore 25 sidewardly.

As shown in FIG. 3, the guide member driving shaft 13 is externally fitted into through holes 34 and 35 which are provided in the distal end block 12 and the tool guide member 5, respectively, so that the two through holes 34 and 35 align with each other in a straight line perpendicular to the longitudinal direction of the distal end part 1a. The guide member driving shaft 13 and the tool guide member 5 are rigidly secured to each other by a cone screw 28 so as not to rotate relative to each other.

Accordingly, as shown in FIG. 4, when the guide member driving lever 21 pivots about the guide member driving shaft 13 in response to the motion of the control wire 22, which is moved back and forth by remote control, the guide member driving shaft 13 is driven to rotate by the pivoting motion of the driving lever 21, and the rotation of the driving shaft 13 is transmitted directly to the tool guide member 5, causing the tool guide member 5 to pivot in the longitudinal direction of the distal end part 1a.

When the control wire 22 is pulled to the full from the control part 3, the guide member driving lever 21 abuts against a step portion 33 formed on a side surface of the guide member driving chamber 20 in the distal end block 12, as shown by the two-dot chain line in FIG. 5. Thus, the guide member driving lever 21 is prevented from pivoting further.

Consequently, the tool guide member 5 is prevented from being excessively erected. Therefore, there is no likelihood of the tool 100 being held between the tool guide member 5 and the distal end block 12 (i.e., in the space A), causing an increase in the resistance to the projection of the tool 100.

Further, a stopper pin 31 is provided between the inner and outer walls 14 and 15 to limit the pivoting range of the tool guide member 5. For example, the stopper pin 31 may project from the inner wall 14, as shown in FIG. 5. The tool guide member 5 is prevented from being excessively flattened by abutting against the stopper pin 31.

In addition, as shown in FIG. 3, an O-ring 29 is fitted on the guide member driving shaft 13 to seal the boundary between the driving shaft 13 and the outer wall 15, thereby isolating the guide member driving chamber 20 from the tool guide member 5 side. The outer opening of the guide member driving chamber 20 is closed with a cover 30 for sealing in a watertight manner. Accordingly, no mucus or blood can externally enter the guide member driving chamber 20, and there is no possibility of the control wire 22 being contaminated with mucus or blood.

According to the present invention, a pair of inner and outer walls which are in contact with both side surfaces of the tool guide member are formed at the distal end of the insert part of the endoscope, and the distal end portion of the control wire is disposed at the outside of the outer wall. Accordingly, even when a tool with a thin distal end is used, it can be smoothly projected along the tool guide member without getting caught on the control wire. Further, since the tool guide member can be disposed close to the viewing window, it is possible to guide a tool with ease while observing it in the central portion of the observation field of view. In addition, the control wire accommodating portion can be readily sealed so that the control wire will not be contaminated with mucus or blood.

while the invention has been described by reference to a specific embodiment chosen for purposes of illustration, it should be apparent that numerous modifications could be made thereto by those skilled in the art without departing from the basic concept and scope of the invention.

I claim:

1. An endoscope a comprising viewing window disposed on one side portion of a distal end of an insert part of said endoscope, and a tool guide member disposed on an other side portion of said insert part so as to be pivotable in a longitudinal direction of said insert part by remote control to change a direction of projection of a tool for an endoscopic procedure, said tool projecting outwardly from said distal end of said insert part;

a pair of inner and outer walls formed on said distal end of said insert part so as to be in contact with two side surfaces of said tool guide member;

a control wire driven to move back and forth by remote control, a distal end of said control wire being disposed at an outside of said outer wall; and a driving force transmitting member disposed to extend through said outer wall so as to transmit movement of said control wire to said tool guide member.

2. An endoscope according to claim 1, said driving force transmitting member being disposed in a recess formed on said outside of said outer wall.

3. An endoscope according to claim 2, said driving force transmitting member comprising:

a shaft portion extending through said outer wall from said recess and connected to said tool guide member at an inside of said outer wall, and a lever portion connected to said distal end of said control wire to pivot about said shaft portion in said recess in response to said movement of said control wire, thereby driving said shaft portion to rotate to cause said tool guide member to pivot about said shaft portion.

4. An endoscope according to claim 3, said shaft portion and said lever portion of said driving force transmitting member being rigidly connected together so as not to rotate relative to each other.

5. An endoscope according to claim 3, said control wire comprising a pin connected to said distal end to define a T-shape with said distal end, said lever portion of said driving force transmitting member comprising a bore provided in an end portion of said lever portion, said pin being insertable into said bore, and said end portion of said lever portion being provided with a groove for avoiding interference with said control wire.

6. An endoscope according to claim 3, wherein, when said control wire is pulled by remote control to a predetermined position, said lever portion of said driving force transmitting member abuts against a side surface of said recess, thereby preventing said lever portion from further pivoting.

7. An endoscope according to claim 3, further comprising:

a stopper positioned so that said tool guide member abuts against said stopper to prevent said tool guide member from pivoting beyond a limit position when said control wire is pushed by remote control to a predetermined position.

8. An endoscope according to claim 3, further comprising:

means for sealing a boundary between said shaft portion of said driving force transmitting member and said outer wall; and a cover for closing an outer opening of said recess in a watertight manner, thereby preventing water from entering said recess.

9. A distal end portion of an endoscope having a control part, comprising:

a distal end body having a recess defined by first and second walls, said first and second walls extending parallel to each other in an insert direction of said endoscope;

a hole extending perpendicularly through said first wall;

an axial member rotatably inserted into said hole and protruding outside from said first wall;

a tool guide member disposed in said recess, said tool guide member being fixed to said axial member;

a driving force transmitting member disposed outside of said first wall and fixed to said axial member; and a control wire extending from said control part to said distal end body and connected to said driving force transmitting member;

wherein said driving force transmitting member is driven by said control wire to pivotably move with said axial member.

10. A distal end portion of an endoscope according to claim 9, further comprising a viewing window disposed in a side surface of said distal end body, so that a tool projected along said tool guide member can be observed through said viewing window.

11. A distal end portion of an endoscope according to claim 10, wherein said first and second walls are formed so that outer ends are approximately flush with a surface of said viewing window.

12. An endoscope according to claim 3, said shaft portion and said tool guide member being formed from discrete parts rigidly connected together so as not to rotate relative to each other.

* * * * *

UNITED STATES PATENT AND TRADEMARK OFFICE
CERTIFICATE OF CORRECTION

PATENT NO. : 5,562,600
DATED : October 8, 1996
INVENTOR(S) : Shinichi MATSUNO

It is certified that error appears in the above-indentified patent and that said Letters Patent is hereby corrected as shown below:

At column 5, line 37 (claim 1, line 1), change "a comprising" to ---comprising: a---.

Signed and Sealed this

Twenty-second Day of July, 1997

Attest:

BRUCE LEHMAN

Attesting Officer

Commissioner of Patents and Trademarks